(12) United States Patent
Yamamoto et al.

(10) Patent No.: US 7,064,560 B2
(45) Date of Patent: Jun. 20, 2006

(54) LIQUID STATE DETECTING ELEMENT AND LIQUID STATE DETECTING SENSOR

(75) Inventors: Takashi Yamamoto, Niwa-gun (JP); Shinichi Hayashi, Mizunami (JP); Masaru Kondo, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/029,021

(22) Filed: Jan. 5, 2005

(65) Prior Publication Data

US 2005/0150292 A1 Jul. 14, 2005

(30) Foreign Application Priority Data

Jan. 6, 2004 (JP) .................. P.2004-001249

(51) Int. Cl.
*G01R 27/26* (2006.01)

(52) U.S. Cl. .................. 324/663; 73/304 C; 73/304 R

(58) Field of Classification Search .............. 73/304 C, 73/304 R; 324/663
See application file for complete search history.

(56) References Cited

U.S. PATENT DOCUMENTS

| | | | |
|---|---|---|---|
| 2,864,981 A | * | 12/1958 | De Giers .................. 361/284 |
| 4,412,270 A | * | 10/1983 | Weitz et al. .............. 361/284 |
| 4,467,646 A | * | 8/1984 | Berryman et al. ........ 73/304 C |
| 4,806,847 A | * | 2/1989 | Atherton et al. .......... 73/304 C |
| 5,929,754 A | * | 7/1999 | Park et al. ................. 340/439 |
| 6,459,995 B1 | * | 10/2002 | Collister ..................... 702/23 |
| 6,705,162 B1 | * | 3/2004 | Amoretti ................. 73/304 C |

FOREIGN PATENT DOCUMENTS

JP 04258725 * 9/1992

* cited by examiner

*Primary Examiner*—Anjan Deb
*Assistant Examiner*—Jeff Natalini
(74) *Attorney, Agent, or Firm*—Stites & Harbison PLLC; Ross F. Hunt, Jr.

(57) ABSTRACT

A liquid state detecting element comprising: a film portion made of a flexible insulating material and extending in a longitudinal direction; and a pair of detecting electrodes juxtaposed to each other on a layer of said film portion and extending in said longitudinal direction, in which said detecting electrodes are for being immersed at least partially in a liquid to be measured, so that a state of said measured liquid is detected on a basis of an electrostatic capacity between said pair of detecting electrodes, wherein: said liquid state detecting element further comprises reinforcing portions made of a conductive material and disposed on said layer of said film portion on an outer side of said detecting electrodes; and said reinforcing portions include: a grounding terminal for being connected with a ground line; and a pair of parallel reinforcing portions extending in said longitudinal direction along side edges of said film portion so as to sandwich said pair of detecting electrodes.

12 Claims, 8 Drawing Sheets

UNGROUNDED GND OF REINFORCING PORTIONS

GROUNDED GND OF REINFORCING PORTIONS

LIQUID STATE DETECTING ELEMENT AND LIQUID STATE DETECTING SENSOR

FIELD OF THE INVENTION

The present invention relates to a liquid state detecting element comprising a film portion and a pair of detecting electrodes, which are immersed at least partially in a liquid to be measured, so that the state may be detected on the basis of an electrostatic capacity between the paired detecting electrodes, and to a liquid state detecting sensor provided with such liquid state detecting element.

BACKGROUND OF THE INVENTION

In the prior art, there have been known a liquid state detecting element and a liquid state detecting sensor, which are provided with a pair of detecting electrodes for detecting the state of a liquid on the basis of a variation of an electrostatic capacity between the electrodes.

The liquid state detecting element is exemplified by either the liquid state detecting element, which is configured by forming a pair of detecting electrodes on a printed circuit board, or the liquid state detecting element which is configured by fusing a pair of detecting electrodes with an insulating film (as referred to JP-A-63-079016 (a printed circuit board 1 and a detecting circuit 5) and JP-A-4-258725 (an electrostatic type level sensor)).

Here, the liquid state detecting element configured by using the printed circuit board has a large thickness size for the printed circuit board so that it is not proper for the application demanding a size reduction (or a thickness reduction). However, the liquid state detecting element configured by using the insulating film has a small thickness size so that it can be arranged in a small space and can satisfy the demand for the size reduction (or the thickness reduction).

SUMMARY OF THE INVENTION

However, the insulating film is characterized to have a flexibility so that it has a far lower rigidity than that of the printed circuit board. Only the provision of the paired detecting electrodes, as disclosed in JP-A-4-258725 (an electrostatic type level sensor), leaves such a problem unsolved that a warping deformation is liable to occur in a longitudinal direction. Especially in case the liquid state detecting element is attached to the oil tank of an automobile and is erected for use in the oil tank, the aforementioned warping deformation is easily increased by the influences of the vibrations of the automobile. If the liquid state detecting element (specifically the insulating film) is deformed, the distance between the detecting electrodes to be arranged in the insulating film varies. The varying characteristics of the electrostatic capacity to the change in the liquid state exhibit those different from the changing characteristics of the initial shape before the deformation. Therefore, an error may occur in the detection result of the liquid state.

On the other hand, the liquid state detecting element is frequently used by configuring the liquid state detecting sensor together with a casing made of a resin or the like and a supporting member for supporting the liquid state detecting element. This liquid state detecting sensor is used for an application to detect a liquid surface level (i.e., the quantity of a liquid) or to detect the deterioration of the liquid.

In this liquid state detecting sensor, however, the casing is the supporting member is arranged around or near the liquid state detecting element. Therefore, the parasitic capacity of the casing or the supporting member may adversely affect the precise measurement of the electrostatic capacity between the detecting electrodes thereby to cause an error in the detection result of the liquid state. Here, the parasitic capacity of the casing or the supporting member is the capacity which is excessively generated at the time of measuring the electrostatic capacity between the detecting electrodes by the dielectric constant belonging to the material itself making the casing or the supporting member.

Therefore, the present invention has been conceived in view of those problems and has an object to provide a liquid state detecting element which is provided a pair of detecting electrodes arranged in a flexible film portion, which is hard to make a detection error due to the warping deformation of a film portion, and which is hard to make a detection error due to a substance other than a liquid to be measured, and a liquid state detecting sensor which is provided with such liquid state detecting element.

In order to achieve the above-specified object, according to the invention, there is provided a liquid state detecting element comprising: a film portion made of a flexible insulating material for extending in a longitudinal direction; and a pair of detecting electrodes juxtaposed to each other on the same layer of the film portion and extending in the longitudinal direction, wherein the detecting electrodes are immersed at least partially in a liquid to be measured, so that the state of the measured liquid is detected on the basis of an electrostatic capacity between the paired detecting electrodes, characterized: by further comprising reinforcing portions made of a conductive material and disposed on the layer of the film portion on the outer side of the detecting electrodes; and in that the reinforcing portions include: a grounding terminal to be connected with a ground line; and a pair of parallel reinforcing portions extending in the longitudinal direction along the side edges of the film portion so as to sandwich the paired detecting electrodes.

In this liquid state detecting element, the film portion is provided with the reinforcing portions made of the conductive material, and especially the paired parallel reinforcing portions composing the reinforcing portions are so arranged along the side edges of the film portion as to sandwich the paired detecting electrodes. As a result, the film portion becomes hard to warp and deform with respect to the longitudinal direction thereby to make it hard for the distance between the paired detecting electrodes to vary. Thus, the distance between the detecting electrodes becomes hard to vary so that the varying characteristics of the electrostatic capacity relative to the change in the liquid state can be prevented from becoming different from the changing characteristics of the initial shape. As a result, it is possible to suppress the occurrence of errors in the liquid state detection.

Moreover, the reinforcing portions are made of the conductive material and are provided with the grounding terminal portion. By grounding (or electrically connecting) the grounding terminal portion to the ground line, therefore, it is possible to change the distribution state of the lines of electric force from one detecting electrode to the other detecting electrode. Specifically, the reinforcing portions connected with the ground potential are arranged in the film portion on the outer side than the detecting electrodes thereby to generate the lines of electric line to be inputted/outputted between the detecting electrodes and the reinforcing portions. Therefore, the distribution of the lines of electric force between the detecting electrodes can be changed to become narrow.

As a result, even in case the liquid state detecting element is arranged in the casing or supported by the supporting member, for example, the electrostatic capacity between the paired detecting electrodes can be prevented from being varied by the influences of the parasitic capacity of the casing or the supporting member.

In other words, this liquid state detecting element is provided with the grounded reinforcing portions. Therefore, the electrostatic capacity of the detecting electrodes easily varies according to the situation change (e.g., the change in the dielectric constant) in the area near the liquid state detecting element so that the electrostatic capacity of the detecting electrodes becomes hard to vary against the situation change (e.g., the change in the dielectric constant) in the area apart from the element itself.

In the liquid state detecting element, there fore, the electrostatic capacity becomes easy to vary according to the measured liquid arranged in the near area so that the detection precision of the liquid state can be improved. Moreover, the liquid state detecting element becomes hard to be influenced by the substance (e.g., the casing) arranged in a remote area. On the detecting electrodes, therefore, the parasitic capacity to be established from the substance other than the other detecting electrode can be reduced to suppress the detection errors of the liquid state. Especially in the invention, the paired parallel reinforcing portions arranged to sandwich the paired detecting electrodes with a view to preventing the warping deformation of the film portion are connected with the ground potential so that they may also function as guard electrodes. Thus, the measurement precision of the electrostatic capacity between the detecting electrodes can be enhanced to enhance the detection precision of the liquid state effectively.

The liquid state to be detected by the liquid state detecting element is exemplified by by the liquid state, in which the electrostatic capacity between the detecting electrodes varies according to the variation of the dielectric constant due to the change in the properties of the liquid itself or the variation of the dielectric constant due to the presence/absence of the liquid, such as the deteriorated state of the liquid (e.g., the deteriorated state of the oil), the level state of the liquid surface (e.g., the liquid quantity), or the concentration of the liquid.

In the liquid state detecting element, the parallel reinforcing portions of the reinforcing portions is preferably formed such that the width size in a width direction perpendicular to the longitudinal direction is made larger than the width size of the detecting electrodes.

In other words, by retaining the large width size of the parallel reinforcing portions, the physical strength as the reinforcing portions can be augmented to suppress more properly the occurrence of the detection errors due to the warping deformation of the film portion.

By retaining the large width size of the parallel reinforcing portions, moreover, the electric shielding effect of the parasitic capacity by the substance other than the measured liquid in the detecting electrodes can be augmented to improve the detection precision of the liquid state.

In the liquid state detecting element, the reinforcing portions preferably include a connecting reinforcing portion for connecting the individual one-end portions of the paired parallel reinforcing portions.

Specifically, the film portion can be effectively prevented from being deformed in the widthwise direction, by providing the connecting reinforcing portion for connecting the one-end portions of the two detecting electrodes as the reinforcing portions in addition to the paired parallel reinforcing portions.

As a result, the distance between the detecting electrodes can be prevented from varying, and the varying characteristics of the electrostatic capacity between the detecting electrodes from the change in the liquid state can be prevented from exhibiting the varying characteristic different from the varying characteristics in the initial distance between the detecting electrodes thereby to suppress any error in the detection result of the liquid state.

In the liquid state detecting element, the detecting electrodes and the reinforcing portions are preferably made of conductive materials of the same kind.

In case the detecting electrodes and the reinforcing portions are made of the common conductive material, at the process for manufacturing the liquid state detecting element, the step of forming the detecting electrodes and the step of forming the reinforcing portions can be executed not at the different steps but at the common step thereby to form the detecting electrodes and the reinforcing portions at the same time.

The liquid state detecting element preferably further comprises a pair of reference electrodes juxtaposed to each other on the same layer of the film portion and arranged at a position different in the longitudinal direction from the arranging position of the paired detecting electrodes, and the paired parallel reinforcing portions may be disposed to sandwich the paired reference electrodes.

Here, a liquid state detecting element comprises the paired reference electrodes separately of the paired detecting electrodes so that it detects the liquid state on the basis of both the electrostatic capacity between the detecting electrodes and the electrostatic capacity between the reference electrodes. In case these reference electrodes are disposed integrally with the film portion having the detecting electrodes, moreover, the measurement precision of the electrostatic capacity between the reference electrodes may drop to cause errors in the detection precision in the liquid state, if the distance between the reference electrodes is varied by the warping deformation of the film portion.

In the invention, on the contrary, the parallel reinforcing portions for suppressing the warping deformation of the film portion are arranged not only to clamp the paired detecting electrodes but also the paired reference electrodes. As a result, the distance not only between the detecting electrodes but also between the reference electrodes can be prevented from varying to enhance the detection precision of the case, in which the liquid state is detected on the basis of the electrostatic capacity between the detecting electrodes and the electrostatic capacity between the reference electrodes.

In order to achieve the above-specified object, according to the invention, there is provided a liquid state detecting sensor comprising: a liquid state detecting element including: a film portion made of a flexible insulating material for extending in a longitudinal direction; a pair of detecting electrodes juxtaposed to each other on the same layer of the film portion and extending in the longitudinal direction; and reinforcing portions made of a conductive material and disposed on the layer of the film portion on the outer side than the detecting electrodes; and a supporting member for supporting the liquid state detecting element, wherein, by immersing at least a portion of the liquid state detecting element in a liquid to be measured, the detecting electrodes are immersed at least partially in the measured liquid, so that the state of the measured liquid is detected on the basis of an electrostatic capacity between the paired detecting electrodes, characterized: in that the supporting member includes supporting portions for supporting the surface and back face of the film portion, whereby the liquid state detecting element is supported by arranging a pair of parallel reinforcing portions included in the film portion, at least partially overlapped by the supporting portions.

The liquid state detecting sensor is provided with the aforementioned liquid state detecting element as the liquid state detecting element. Therefore, the liquid state detecting sensor is hard to have the detection error accompanying the warping deformation of the liquid state detecting element (or the film portion) so that it can exhibit the effect that it is hard to have the detection error due to the influences of the parasitic capacity of the supporting member.

Moreover, this liquid state detecting sensor is characterized by comprising: the supporting portions for supporting the surface and the back face of the film portion as the supporting member for supporting the liquid state detecting element; and the supporting member for supporting the liquid state detecting element by arranging the paired parallel reinforcing portions arranged in the film portion, at least partially overlapped by the supporting portions. In short, in this liquid state detecting sensor, the liquid state detecting element is so sandwiched between the supporting portions that the paired parallel reinforcing portions having the enhanced rigidity in the liquid state detecting element are arranged at least partially overlapped by the supporting portions of the supporting member.

As a result, the liquid state detecting sensor can have its liquid state detecting element stably supported, when used, on the supporting member so that it can suppress the warping deformation of the liquid state detecting element stably in combination with the effect of the rigidity of the film portion, as enhanced by the reinforcing portions. Moreover, this liquid state detecting sensor has a configuration, in which the liquid state detecting element is hard to come out of the supporting portions of the supporting member, so that it can suppress the detection errors due to the falling of the liquid state detecting element.

The mode for supporting the surface and the back face of the film portion of the liquid state detecting element by the supporting portions of the supporting member is exemplified by the mode, in which the supporting portions clamp the liquid state detecting element (or the film portion) from the two film faces while contacting with the film portion. In another mode, the supporting portions can be provided with clearance portions having a larger clearance size than the thickness size of the liquid state detecting element so that the liquid state detecting element (or the film portion) is fitted in the clearance portions. In short, the supporting portions of the supporting member may take any shape but should not be limited to a specific shape, if they can confine the moving range of the liquid state detecting element within such a range as raises no error in the detection precision.

In the liquid state detecting sensor, preferably, the supporting member includes erected pins, and the liquid state detecting element includes through holes extending through the film portion, whereby the liquid state detecting element is positioned on the supporting member by inserting the pins into the through holes.

In this liquid state detecting sensor, the liquid state detecting element is positioned in the supporting member by inserting the pins formed on the supporting member into the through holes formed in the film portion, so that the paired detecting electrodes for detecting the liquid state can be reliably positioned with respect to the supporting member. In the mass-production case of the liquid state detecting sensor for supporting the liquid state detecting element by using the supporting member, therefore, it is possible to suppress the dispersion of the arrangement of the detecting electrodes for detecting the liquid state individually in the supporting member, and accordingly to suppress the dispersion of the liquid state detecting sensors of the common product number individually in the detection precision.

BRIEF DESCRIPTION OF THE DRAWINGS

Of FIGS. 7A and 7B presenting explanatory views of the level detecting element according to Embodiment 2.

Figure 1:
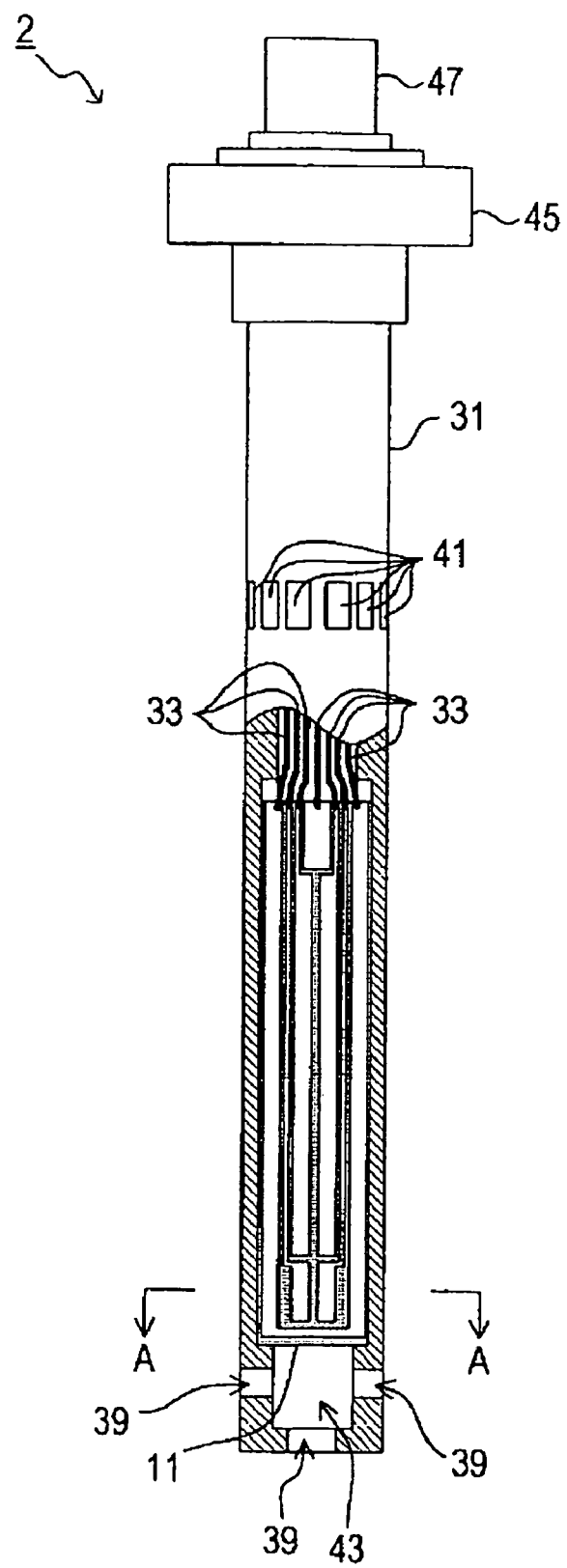
FIG. 1 is a partially broken sectional view of an oil level sensor according to Embodiment 1.

DESCRIPTION OF REFERENCE NUMERALS AND SIGNS 1, 100: OIL LEVEL SENSOR
11, 131: LEVEL DETECTING ELEMENT
13, 133: DETECTING ELECTRODES
17, 139: REFERENCE ELECTRODES
21, 137: REINFORCING PORTIONS
23, 153: CONNECTING REINFORCING PORTION
25, 151: PARALLEL REINFORCING PORTIONS
26, 155: GROUNDING TERMINAL
29, 132: FILM PORTION
31: CASING (SUPPORTING MEMBER)
43: INTERNAL SPACE
49, 181: SUPPORTING PORTIONS
111: SENSOR CAP
171: UPPER THROUGH HOLE
173: CENTRAL THROUGH HOLES
180: SUPPORTING MEMBER
183: UPPER SUPPORTING PIN
185: CENTRAL SUPPORTING PINS

DETAILED DESCRIPTION OF THE INVENTION

Embodiments of the invention will be described with reference to the accompanying drawings.

[Embodiment 1]

This embodiment will be described on an oil level sensor 1, which is disposed in an oil reserving oil tank for detecting the oil level (or the liquid surface level) in the oil tank. This oil level varies with the content of the oil in the oil tank.

FIG. 1 is a partially broken sectional view of the oil level sensor 1 and shows the internal structure of a portion of the oil level sensor 1.

The oil level sensor 1 is constructed to include a level detecting element 11 having a pair of detecting electrodes, and a casing 31 for housing and positioning the level detecting element 11.

In FIG. 1, a portion of the oil level sensor 1 and the level detecting element 11 are presented in section so as to present the internal structure of that portion of the casing 31, in which the level detecting element 11 is arranged.

First of all, the description is made on the level detecting element 11 of the oil level sensor 1.

Figure 2:
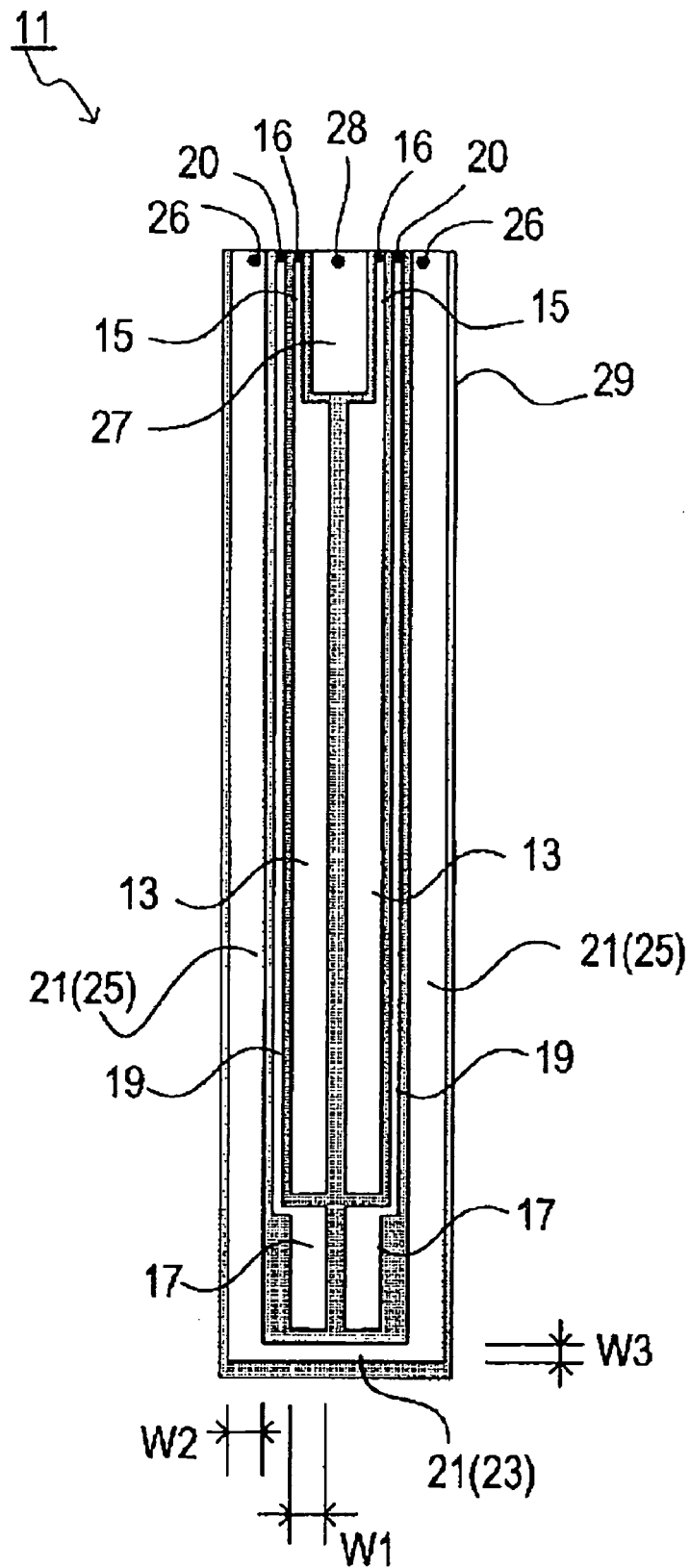
FIG. 2 is an explanatory view showing a level detecting element according to Embodiment 1.

FIG. 2 is an explanatory view (or a sectional view) of the level detecting element 11.

The level detecting element 11 is provided with: a rectangular film portion 29 made of a flexible insulating material (e.g., polyimide); a variety of electrodes (including a pair of detecting electrodes 13, a pair of reference electrodes 17, and a grounding electrode 27) buried in the film portion 29 and made of a conductive material (e.g., copper); and reinforcing portions 21 formed in the film portion 29 on the outer side portions of the various electrodes. Specifically, the paired detecting electrodes 13, the paired reference electrodes 17, the grounding electrode 27 and the reinforcing portions 21 are sealed with two films of polyimide and are juxtaposed on the common film of the film portion 29, which are formed by laminating two films.

The paired detecting electrodes 13 are individually formed in a long shape and are juxtaposed to each other and in parallel with the longitudinal direction. The paired detecting electrodes 13 thus arranged in parallel are characterized in that the electrostatic capacity between the detecting electrodes varies with the dielectric constant of the substance arranged therearound. As a result, the electrostatic capacity between the paired detecting electrodes 13 (as will also be called the "electrostatic capacity of the detecting electrodes 13") varies with the ratio of the immersed portion of the longitudinal size of the detecting electrodes 13 in the oil (i.e., the oil immersed ratio of the detecting electrodes 13).

In short, a correlation exists between the electrostatic capacity of the detecting electrodes 13 and the oil immersed ratio of the detecting electrodes 13 so that the oil immersed ratio of the detecting electrodes 13 can be defined on the basis of the electrostatic capacity of the detecting electrodes 13. As a result, the level detecting element 11 having the detecting electrodes 13 can be utilized for detecting the oil level (or the liquid surface level) in the installation area (i.e., the inside of the oil tank).

The paired reference electrodes 17 are also formed into in a long shape, although shorter than the detecting electrodes 13, and are so juxtaposed to each other and in parallel with the longitudinal direction as are located closer to the leading end side (i.e., on the lower side, as shown) of the film portion 29 than the detecting electrodes 13. The paired reference electrodes 17 thus juxtaposed are characterized like the detecting electrodes 13 in that the electrostatic capacity between the reference electrodes varies with the dielectric constant of the substance arranged therearound. Moreover, the reference electrodes 17 are formed on the leading end side of the detecting electrodes 13 and arranged on the bottom side in the oil tank so that their entirety is immersed at all times in the oil. As a result, the electrostatic capacity between the paired reference electrodes 17 (as will also be called the "electrostatic capacity of the reference electrodes 17") varies exclusively in dependence on the dielectric constant of the oil.

In case the oil changes in properties due to deterioration or in case oil of a different kind is additionally reserved, the dielectric constant of the oil changes even for the same oil level. Therefore, the detection precision drops if the oil level is detected exclusively on the basis of the electrostatic capacity of the detecting electrodes 13.

In this embodiment, therefore, the electrostatic capacity detected by using the reference electrodes 17 is employed as a reference value, and the oil level is detected by using both the electrostatic capacity of the reference value and the electrostatic capacity of the detecting electrodes 13. As a result, the oil level can be properly detected even in case the dielectric constant of the oil has changed due to the deterioration of the oil.

Here, the detecting electrodes 13 and the reference electrodes 17 are individually formed to have a thickness size of 50 [μm] and a width size W1 of 2.0 [mm].

On the other hand, the level detecting element 11 is provided with: two level lead portions 15 extended from the individual trailing end portions (or the upper side end portions, as shown in FIG. 2) of the two detecting electrodes 13 to the trailing end of the film portion 29; and two reference lead portions 19 extended from the individual trailing end portions (or the upper side end portions, as shown in FIG. 2) of the two reference electrodes 17 to the trailing end of the film portion 29.

The level lead portions 15 are provided with connecting terminal portions 16 on their own trailing end portions, and the reference lead portions 19 are provided with connecting terminal portions 20 on their own trailing end portions. The level lead portions 15 and the reference lead portions 19 are connected through metallic lead members 33 (as referred to FIG. 1) with various external devices disposed outside of the oil level sensor 1, by connecting the connecting terminal portions 16 and the connecting terminal portions 20 individually with the metallic lead members 33 when the level detecting element 11 is supported by the casing 31.

The grounding electrode 27 is formed closer to the trailing end side (or on the upper side, as shown) of the film portion 29 than the detecting electrodes 13 and at the position which is defined between the two level lead portions 15. Moreover, the grounding electrode 27 is provided with a grounding terminal portion 28 on its own trailing end portion. The grounding electrode 27 is connected through the metallic lead members 33 with a ground line (or a grounding potential line), by connecting the grounding terminal portion 28 with the metallic lead members 33 (as referred to FIG. 1) when the level detecting element 11 is supported by the casing 31.

When the grounding electrode 27 is grounded to the ground line, the electrostatic capacity between the electrodes of the paired level lead portions 15 becomes small. As a result, the electrostatic capacity of the level lead portions 15 can be prevented from adversely affecting as a stray capacity, when the electrostatic capacity of the detecting electrodes 13 is measured.

The reinforcing portions 21 are made of a conductive material (e.g., copper) and are formed in the film portion 29 at the portions on the outer sides of the detecting electrodes 13 and the reference electrodes 17. Moreover, the reinforcing portions 21 are provided with: a pair of parallel reinforcing portions 25 juxtaposed to each other and in parallel with the longitudinal direction of the detecting electrodes 13; and a connecting reinforcing portion 23 formed closer to the leading end side than the reference electrodes 17.

The paired parallel reinforcing portions 25 are arranged in the film portion 29 on the outer sides of the reference electrodes 17 and the reference lead portions 19. Specifically, the paired parallel reinforcing portions 25 are arranged to sandwich the paired detecting electrodes 13, the level lead portions 15, the reference lead portions 19 and the reference electrodes 17 and to extend along the side edges of the film portion 29.

The parallel reinforcing portions 25 of the reinforcing portions 21 are formed to have a thickness size of 50 [μm] and a width size W2 of 2.2 [mm] on the film layer.

The connecting reinforcing portion 23 is so formed to extend in the widthwise direction (or in the transverse direction of FIG. 2) on the film layer of the film portion 29 as to connect the leading end portions of the paired parallel reinforcing portions 25.

The connecting reinforcing portion 23 of the reinforcing portions 21 is formed to have a thickness size of 50 [μm] and a height size W3 of 1.0 [mm], as taken in a direction perpendicular to its own longitudinal direction on the film layer.

The reinforcing portions 21 are provided at the trailing end portions of the parallel reinforcing portions 25 with grounding terminal portions 26 to be connected with the ground line. The reinforcing portions 21 are connected through the metallic lead members 33 with the ground line (or the ground potential line), by connecting the grounding terminal portions 26 with the metallic lead members 33 (as referred to FIG. 1) when the level detecting element 11 is supported by the casing 31.

Here will be described the casing 31 of the oil level sensor 1.

Figure 3:
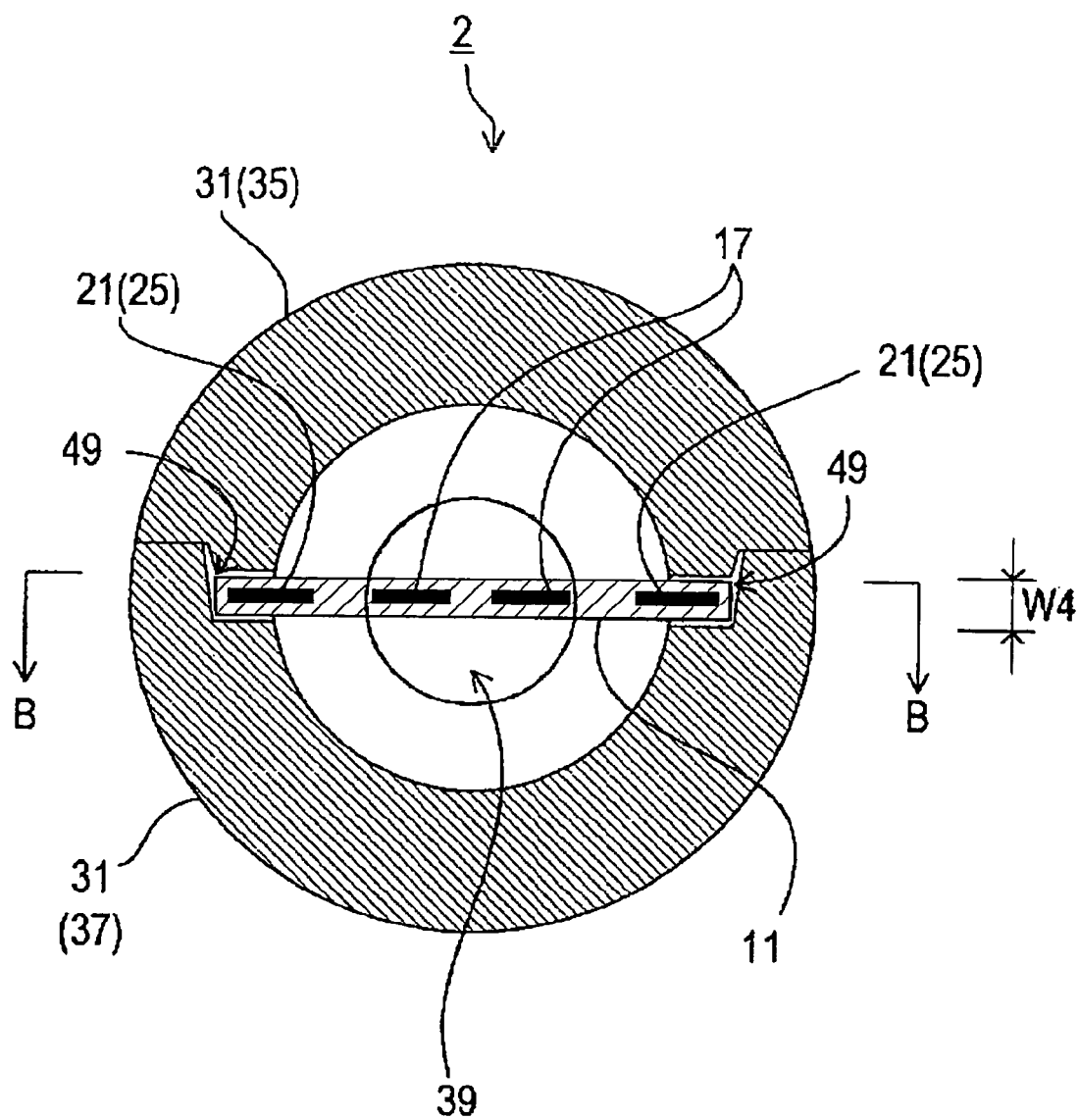
FIG. 3 is a sectional view presenting section A—A of the oil level sensor of FIG. 1.

The sectional view presenting section A—A of the oil level sensor 1 in FIG. 1 is shown in FIG. 3. The sectional view presenting section B—B of the oil level sensor 1 in FIG. 3 corresponds to the broken section portion in FIG. 1.

As shown in FIG. 1 and FIG. 3, the casing 31 is formed into an elongated substantially cylindrical shape extending in the axial direction by combining a first semicircular cylinder member 35 and a second semicircular cylinder member 37, which are made of a synthetic resin (e.g., 6—6 nylon) having an insulating property, and is provided with an internal space 43 for arranging the level detecting element 11 in its own inside.

The casing 31 is provided with: a plurality of leading end side through holes 39 formed on the leading end side (i.e., on the lower side in FIG. 1) of its own axial direction and leading to the internal space 43 from the outside; and a plurality of central side through holes 41 formed in the substantially central portion of its own axial direction and leading to the internal space 43. In short, the casing 31 is so constructed that the substance (e.g., the oil or the air) between its own outside and the internal space 43 may migrate through the leading end side through holes 39 and the central side through holes 41.

These leading end side through holes 39 and central side through holes 41 are formed at uncorresponding positions in the portions around the diametrical direction of the level detecting element 11 being arranged in the casing 11. This arrangement is made to prevent the oil to flow into and out of the inside of the casing 31 from impinging directly on the level detecting element 11 thereby to eliminate the occurrence of detection errors, which might otherwise accompany the instantaneous change in the oil level due to vibrations.

Moreover, the casing 31 is provided, on the trailing end side (i.e., on the upper side in FIG. 1) of its own axial direction, with a flange portion 45 extending radially outward, and a connector portion 47, with which a device side connector leading to the external devices is connected. The flange portion 45 is formed to abut against the outer surface of the oil tank, when the oil level sensor 1 is attached to the oil tank, thereby to determine the direction and position of insertion of the oil level sensor 1 (or the casing 31) in the oil tank. The connector portion 47 is constructed to include metal terminals to be electrically connected with the individual metallic lead members 33, and a connector frame portion shaped to be fitted on the device side connectors. The connector portion 47 is disposed to form current passages leading from the individual electrodes of the level detecting element 11 to the external devices.

The casing 31 is further provided with two supporting portions 49 for clearance spaces between the first semicircular cylinder member 35 and the second semicircular cylinder member 37, as shown in FIG. 3. The supporting members 49 are formed to have a clearance spacing size W4 larger than the thickness size of the level detecting element 11.

The level detecting element 11 is so determined in its arranged position in the internal space 43 of the casing 31 that the two side edge portions in its own widthwise direction are individually arranged in the supporting portions 49.

At this time, the casing 31 arranges the paired parallel reinforcing portions 25 of the level detecting element 11 at least partially overlapped by the supporting portions 49 thereby to position the level detecting element 11 in the internal space 43. As a result, the casing 31 enables the supporting portions 49 to support the stronger portion (or the less deformable portion) of the level detecting element 1. In combination with the effect that the rigidity of the film portion 29 having a flexibility is enhanced by providing the reinforcing portions 21, the casing 31 can prevent the warping deformation of the level detecting element 11 effectively and can prevent the level detecting element 11 from coming out from the supporting portions 49.

Here, the clearance spacing size of the supporting portions 49 is larger than the thickness size of the level detecting element 11. Therefore, the casing 31 clamps the level detecting element 11 in the thickness direction by the supporting portions 49 such that the clearance is established between the inner face of the supporting portions 49 and the outer face of the level detecting element 11, and supports the level detecting element 11 in the widthwise direction by the two supporting portions 49.

When the oil level sensor 1 is arranged in the oil tank or the area to be measured, its internal space 43 is supplied with the oil in the quantity corresponding to the oil level (or the liquid surface level). At this time, the level detecting element 11 is immersed in the oil at a ratio corresponding to the oil level so that the electrostatic capacity of the detecting electrodes 13 indicates a value corresponding to the oil level. On the other hand, the electrostatic capacity of the reference electrodes 17 indicates a value corresponding to the dielectric constant of the oil.

Here, the level detecting element 11 is provided with the reinforcing portions 21 connected (or grounded) with the ground line, so that it can suppress the influences of the parasitic capacity of the casing against the electrostatic capacity of the detecting electrodes 13 and the electrostatic capacity of the reference electrodes 17. Therefore, the level detecting element 11 can detect the oil level precisely while suppressing the occurrence of errors.

The external devices connected with the oil level sensor 1 execute the procedure for deciding the oil level on the basis of the electrostatic capacity of the detecting electrodes 13 and the electrostatic capacity of the reference electrodes 17.

Figure 4:
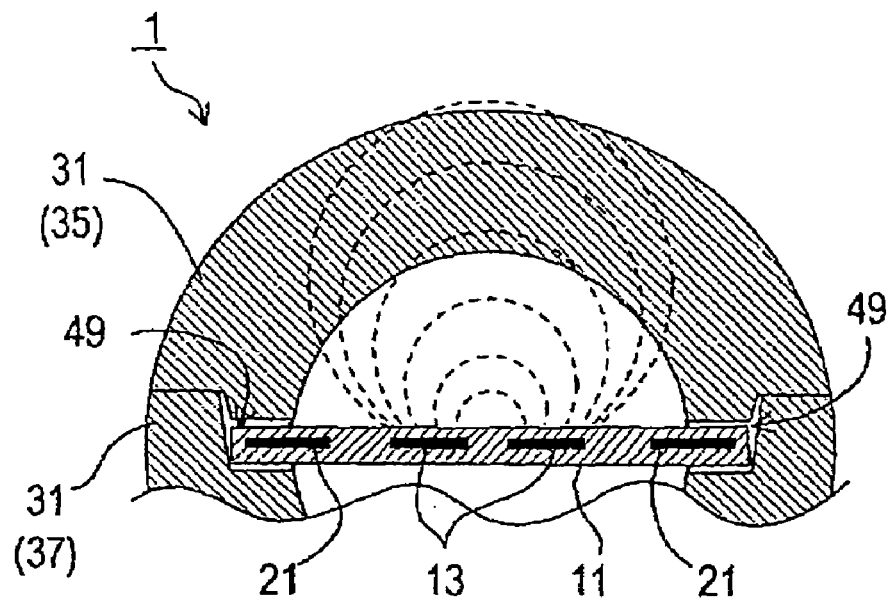
FIG. 4 presents explanatory views schematically presenting the distribution states of lines of electric force emanating from and ending in detecting electrodes in case the level detecting element is arranged in a casing.
Figure 4:
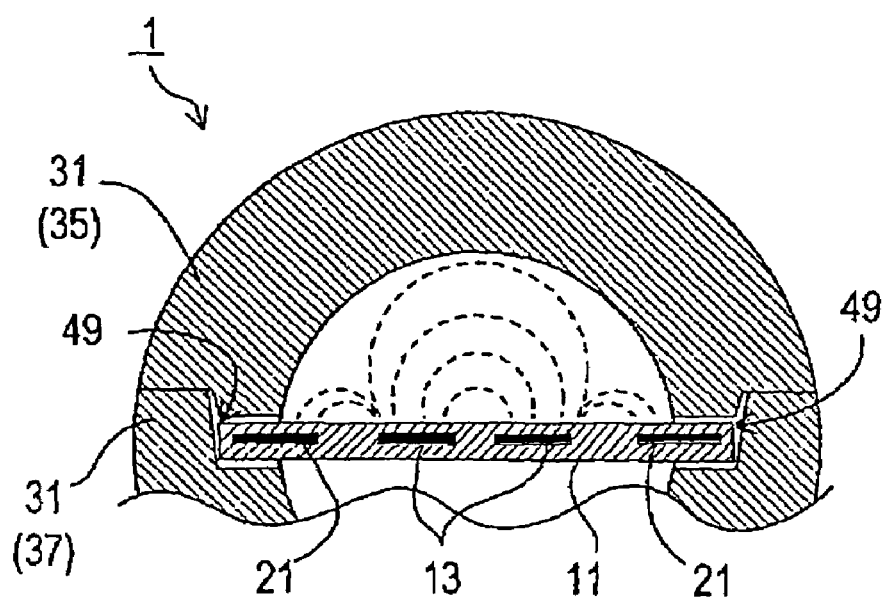

FIG. 4 shows explanatory diagrams, which schematically present the distribution states of lines of electric force to flow into and out of the detecting electrodes 13 in case the level detecting element 11 is arranged in the casing 31.

Here, the distribution state of the lines of electric force in the ungrounded GND state of the reinforcing portions is shown on the upper side of FIG. 4, and the distribution state of the lines of electric force in the grounded GND state of the reinforcing portions is shown on the lower side. In FIG. 4, moreover, the lines of electric force are indicated by broken lines, and the reference lead portions 19 are omitted.

In the ungrounded state GND of the reinforcing portions, as shown in FIG. 4, the lines of electric force emanating from and ending in the detecting electrodes 13 are distributed over a wide area, and some of them enter the casing 31. In the grounded state GND of the reinforcing portions, on the contrary, the lines of electric force to and from the detecting electrodes 13 go partially into and out of the grounded reinforcing portions 21 so that they are narrowed in their distribution range. Thus, the lines of electric force quit the entrance into the casing 31.

Thus, the lines of electric force comes to the state not to pierce the casing 31, so that the electrostatic capacity of the detecting electrodes 13 can be prevented from being influenced by the dielectric constant of the casing 31 thereby to suppress the establishment of the parasitic capacity by the casing 31.

As has been described hereinbefore, the level detecting element 11 of this embodiment is provided with the reinforcing portions 21 so that it has a high strength. Therefore, the level detecting element 11 is characterized in that the film portion 29 is hard to become warped and deformed so that the distance between the paired detecting electrodes 13 and the distance between the paired reference electrodes 17 are individually hard to vary. Thus, the distance between the detecting electrodes is hard to vary so that the characteristics for the electrostatic capacity to vary with respect to the variation of the oil level can be prevented from becoming different from the changing characteristics in the initial shape of the level detecting element 11 thereby to suppress the errors in the oil level detection.

Moreover, the reinforcing portions 21 are made of the conductive material (e.g., copper) and is provided with the grounding terminal portion 26. By grounding (or electrically connecting) the grounding terminal portion 26 with the ground line, therefore, the distribution ranges of the lines of electric force from one detecting electrode 13 to the other detecting electrode 13 and from one reference electrode 17 to the other reference electrode 17 can be so changed that they can become narrower.

Even in case the level detecting element 11 is arranged in the casing 31, therefore, it is possible to prevent the electrostatic capacity between the paired detecting electrodes 13 and the electrostatic capacity between the paired reference electrodes 17 from being varied by the influences of the parasitic capacity of the casing 31.

Thus, the level detecting element 11 of this embodiment becomes such a liquid state detecting element that the detection errors accompanying the warping deformation are hard to occur and that the detection errors are hard to occur with the influences of the substance (of the casing 31) other than the oil or the liquid to be measured.

In the level detecting element 11, moreover, the widthwise size W2 of the parallel reinforcing portions 25 is larger than the widthwise size W1 of the detecting electrodes 13 and the reference electrodes 17. Therefore, a higher strength of the reinforcing portions 21 can be retained to suppress the occurrence of the detection errors, which might otherwise be caused by the warping deformation of the film portion 29.

The parallel reinforcing portions 25 can attain, even in case it has a smaller width size than that of the detecting electrodes 13, the electric shielding effect, and can suppress the influences of the parasitic capacity of the casing 31 thereby to attain an effect to reduce the detection errors.

In the level detecting element 11, moreover, the detecting electrodes 13, the reference electrodes 17 and the reinforcing portions 21 are wholly made of copper, i.e., the conductive material of the same kind. In the process for manufacturing the level detecting element 11, therefore, the step of forming (i.e., etching or printing) the detecting electrodes 13 and the reference electrodes 17 and the step of forming (i.e., etching or printing) the reinforcing portions 21 can be executed not at different steps but at the same step.

As a result, the plural steps in the procedure for manufacturing the level detecting element 11 can be compiled into one step so that the number of steps can be reduced to improve the manufacturing efficiency of the level detecting element 11.

In this embodiment, the detecting electrodes 13 correspond to the detecting electrodes. On the other hand, the casing 31 corresponds to the supporting member.

[Embodiment 2]

Figure 6:
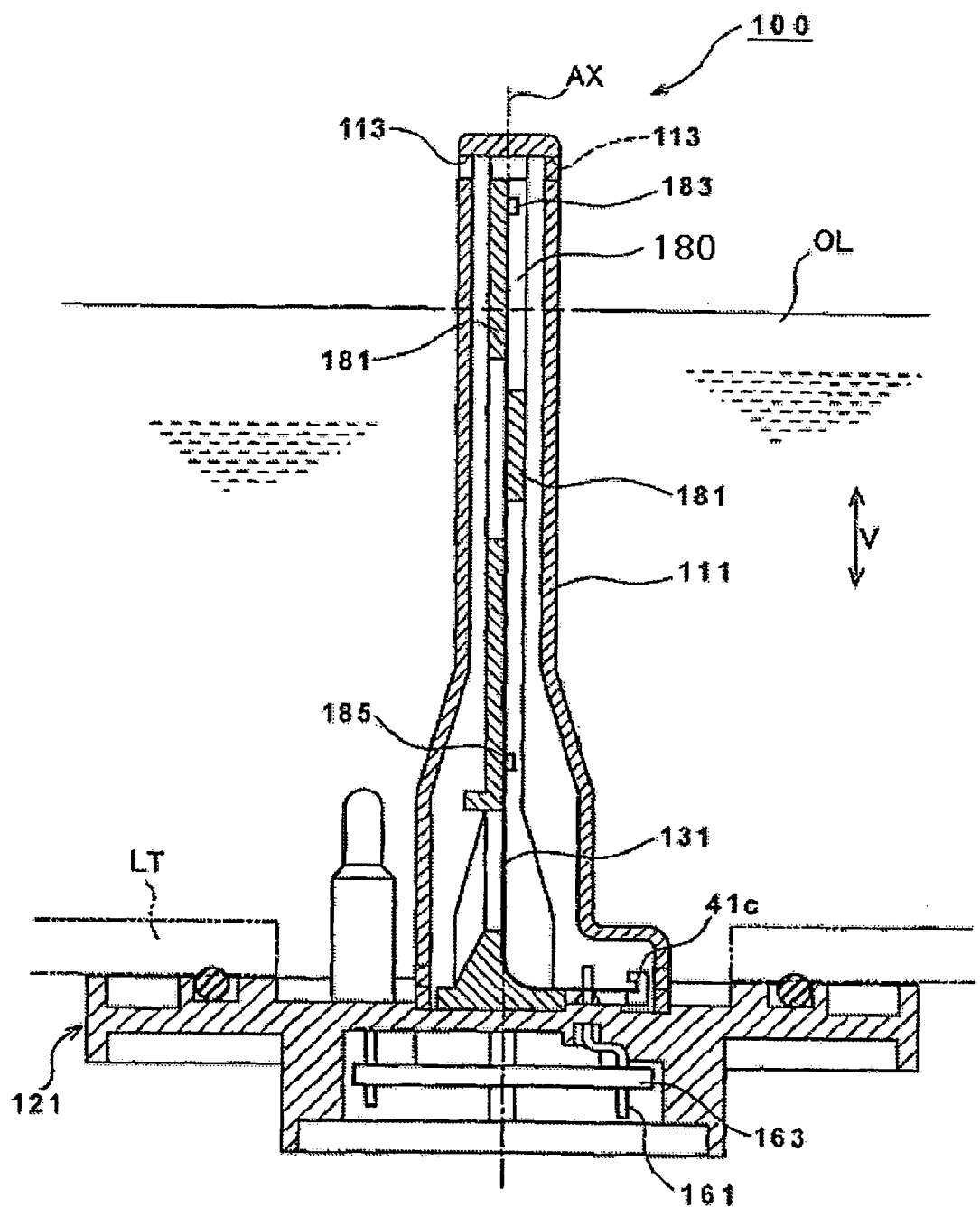
FIG. 6 is an explanatory view of the state, in which the oil level sensor according to Embodiment 2 is attached to the oil tank of an automotive engine.

Here will be described an oil level sensor 100 according to Embodiment 2. As shown in FIG. 6, this oil level sensor 100 is so attached for use to an oil tank bottom portion LT of an automotive engine that its axis is aligned with a vertical direction V and that its leading end is directed upward in the vertical direction. The oil level sensor 100 thus attached is used to detect the level of oil OL.

Figure 5:
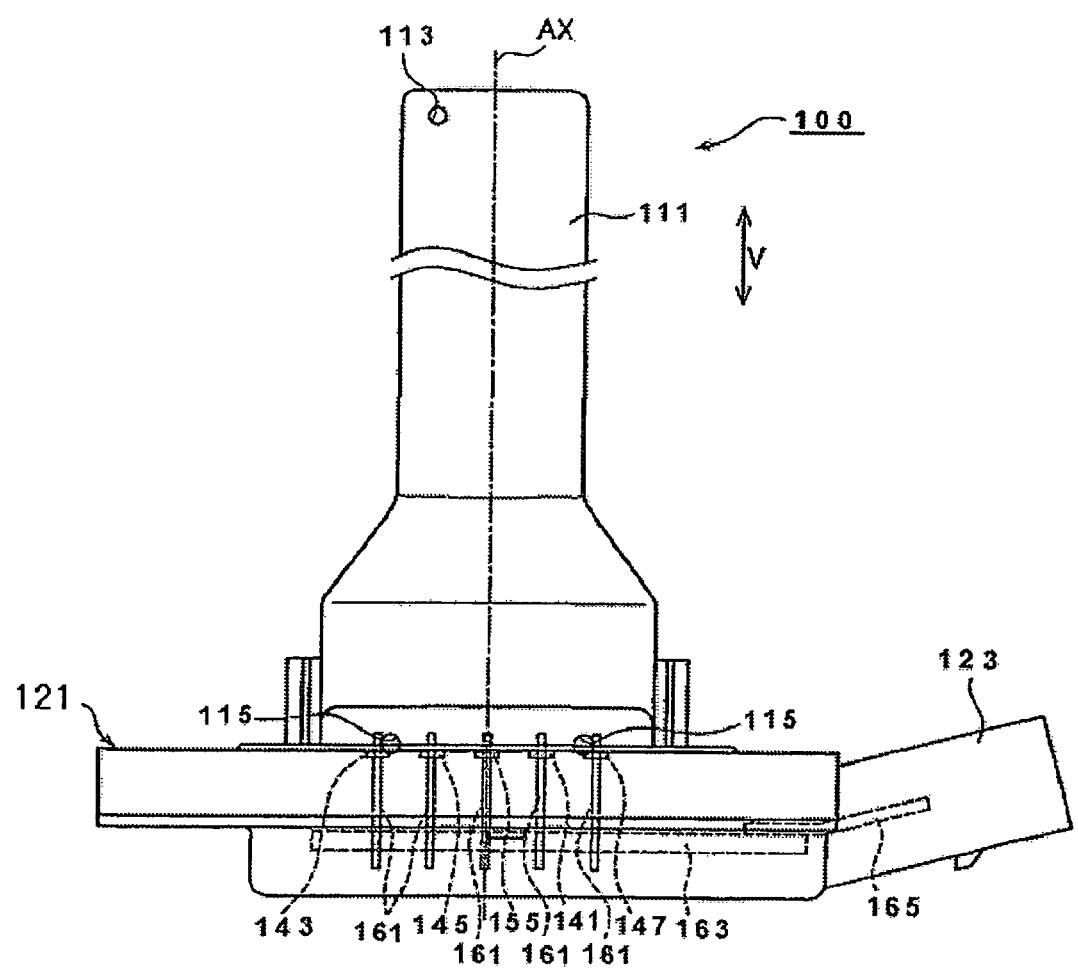
FIG. 5 is a front elevation of an oil level sensor according to Embodiment 2.

As shown in FIG. 5 and FIG. 6, moreover, the oil level sensor 100 includes a base member 121 made of a resin, and a substantially cylindrical sensor cap 111 arranged to protrude from the base member 121. This sensor cap 111 having the hollow structure encloses a level detecting element 131 having a pair of detecting electrodes 133 or the like disposed in a film portion 132, and a supporting member 180 for supporting the level detecting element 131 in the vertical direction. Here, the sensor cap 111 is provided, at its root end portion, with communication holes 115 for establish the communication of the surrounding oil OL with the inside and outside of the sensor cap 111, and, at its leading end portion, with communication holes 113 for the air vent.

The base member 121 supports the supporting member 180 and the sensor cap 111. By fixing the base member 121 on the oil tank bottom portion LT with the supporting member 141 and the sensor cap 111 inserted in the oil tank, the oil level sensor 100 is mounted in the oil tank (as referred to FIG. 6).

Figure 7A:
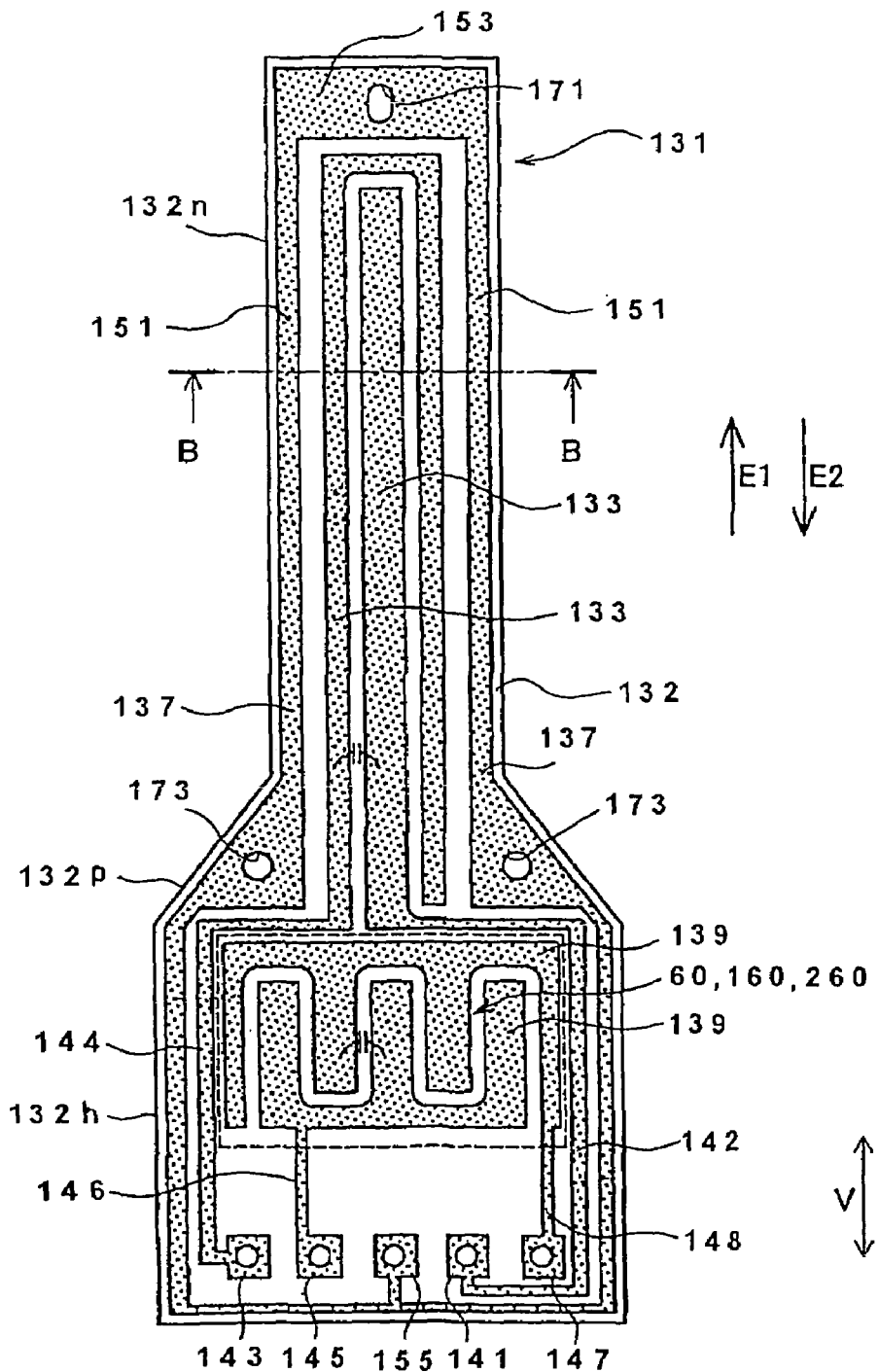
FIG. 7A is a top plan view of the level detecting element.
Figure 7B:
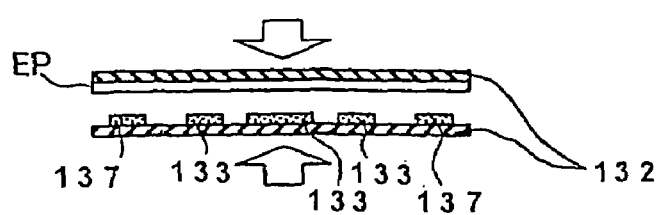
FIG. 7B is an exploded sectional view (i.e., section B—B) of the level detecting element.

Of the oil level sensor 100 according to Embodiment 2, the level detecting element 131 will be described at first with reference to FIGS. 7A and 7B. As shown in FIG. 7A, the level detecting element 131 has the film portion 132 shaped by connecting a first rectangular portion 132h having a larger width, a taper portion 132p having a converging trapezoidal shape and a second rectangular portion 132n having a smaller width sequentially in the recited order in the longitudinal direction from the root end (i.e., the lower end, as shown) to the leading end (i.e., the upper end, as shown). Here, the film portion 132 is made of flexible polyimide like the aforementioned one of Embodiment 1.

This film portion 132 is provided therein with various electrodes (e.g., a pair of detecting electrodes 133 and a pair of reference electrodes 139) made of a conductive material (e.g., copper), and reinforcing portions 137 arranged at the outer side portions of the various electrodes. Specifically, the paired detecting electrodes 133, the paired reference electrodes 139 and the reinforcing portions 137 are sealed with two films of polyimide and are juxtaposed on the same layer of the film portion 132, which is formed by laminating and adhering two films through epoxy resin paste EP (as referred to FIG. 7B).

The paired detecting electrodes 133 are formed to extend in the longitudinal direction of the film portion 133 and are arranged on the second rectangular portion 132$n$ and the taper portion 132$p$ of the film portion 132. Here, one of the paired detecting electrodes 133 is formed to have a straight shape, and the other is formed to have a U-shape. Of the paired detecting electrodes 133, moreover, one is connected with a square-shaped first electrode terminal 141 through a first electrode connecting line 142, and the other is connected with a square-shaped second electrode terminal 143 through a second electrode connecting line 144.

In the film portion 132 closer to the base end side than the detecting electrodes 133, on the other hand, the paired reference electrodes 139 of a comb-tooth shape are so arranged to confront each other through a series of gaps as to mesh with each other. Of the paired detecting electrodes 139, one is connected with a square-shaped first reference electrode terminal 145 through a first reference electrode connecting line 146, and the other is likewise connected with a square-shaped second reference electrode terminal 147 through a second reference electrode connecting line 148.

Here, the principle for detecting the oil level by using both the electrostatic capacity measured at the paired detecting electrodes 133 and the electrostatic capacity measured at the paired reference electrodes 139 is similar to that which has been described in connection with Embodiment 1.

The reinforcing portions 137 are made of a conductive material (e.g., copper) and are formed in the film portion 132 on the outer side portions of the paired detecting electrodes 133 and the paired reference electrodes 139. Moreover, the reinforcing portions 137 are provided with: a pair of parallel reinforcing portions 151 juxtaposed to each other and in parallel with the longitudinal direction of the detecting electrodes 133; and a connecting reinforcing portion 153 formed closer to the leading end side than the detecting electrodes 133. The paired parallel reinforcing portions 151 are arranged to sandwich the paired detecting electrodes 133, the first and second electrode terminals 141 and 143, the first and second electrode connecting lines 142 and 144, the paired reference electrodes 139, the first and second reference electrode terminals 145 and 147, and the first and second reference electrode connecting lines 146 and 148. On the other hand, the connecting reinforcing portion 153 is so formed to extend in the widthwise direction of the film portion 132 as to connect the leading end portions of the paired parallel reinforcing portions 151.

Moreover, the reinforcing portions 137 are provided with a grounding terminal 155, which is formed in a square shape and connected with the ground line. The trailing ends of the paired parallel reinforcing portions 151 are individually connected with the grounding terminal 155. When the level detecting element 131 is assembled with the base member 121, the grounding terminal 155 is connected with wiring members 161, and the reinforcing portions 137 are connected, when used, through the wiring members 161 with the ground line (or the ground potential line).

Near the leading end of the film portion 132 and in the widthwise center portion, there is formed an upper through hole 171 which is formed into an elliptical shape elongated in the longitudinal direction. This upper through hole 171 positions the film portion 132, when this film portion 132 is assembled with the later-described supporting member 180, and to hold the leading end side of the film portion 132 while preventing it from floating. In the taper portion 132$p$, there are formed circular through holes 173 for positioning the film portion 132.

Here is omitted the effect of the provision of the level detecting element 131 according to Embodiment 2 with the reinforcing portions 137, because it is similar to the aforementioned one of Embodiment 1.

Figure 8:
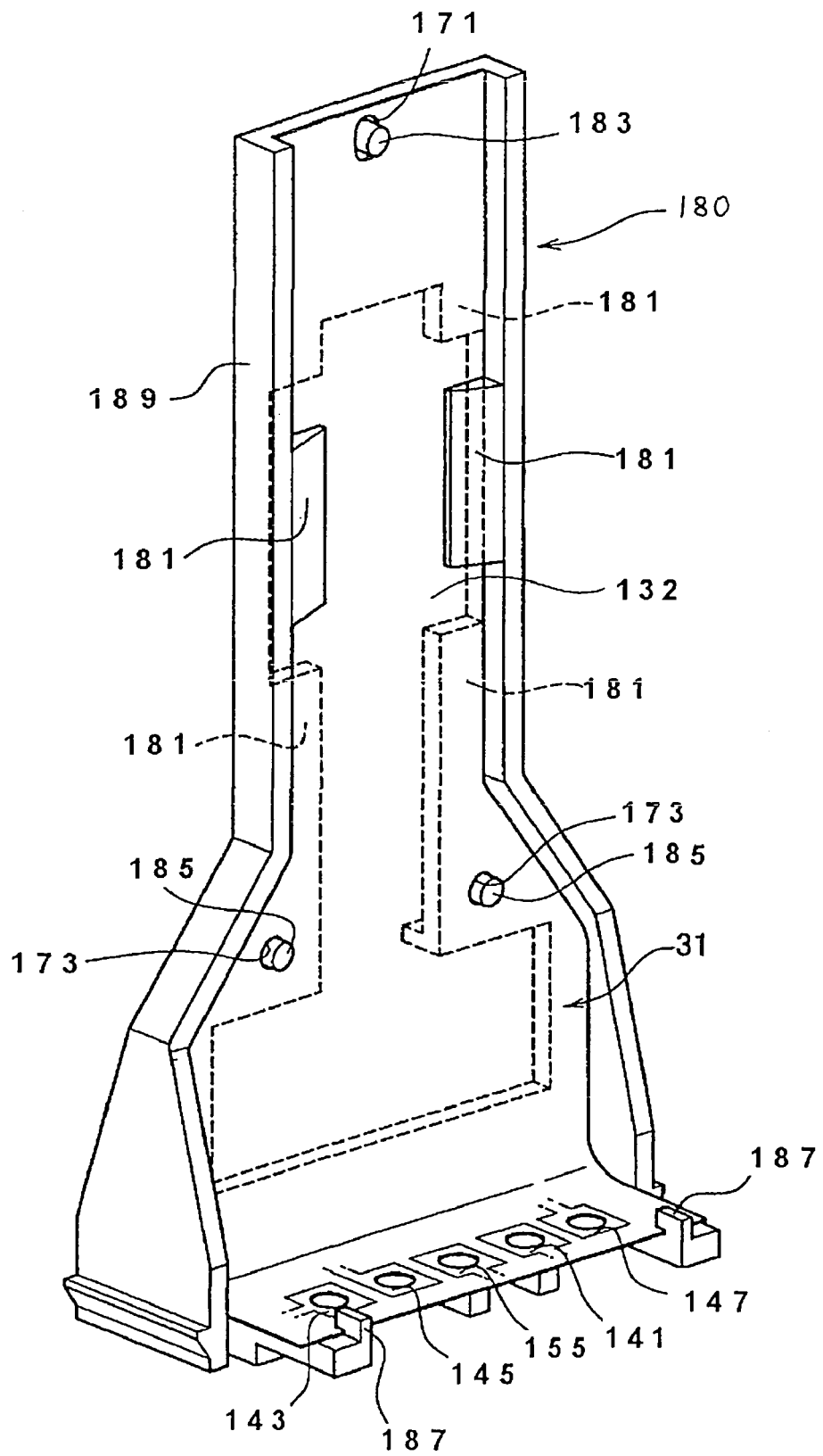
FIG. 8 is a perspective view showing the state, in which the level detecting element is assembled with a support according to Embodiment 2.

The supporting member 180 in the oil level sensor 100 according to Embodiment 2 will be described with reference to FIG. 8. FIG. 8 shows the state, in which the level detecting element 131 is assembled with the supporting member 180. However, the various conductors such as the detecting electrodes 133 or the reinforcing portions 137 of the level detecting element 131 are omitted from FIG. 8, so that the configuration of the supporting member 180 may be easily understood.

This supporting member 180 is made of 66-nylon and has such a frame shape resembling the plan shape of the film portion 132 as to support the peripheral edge of the film portion 132. The supporting member 180 includes: supporting portions 181, which protrude inward from two right and left frame portions 189 for supporting the surface and back close to the side edges of the film portion 132 alternately; an upper supporting pin 183; central portion supporting pins 185; and lower portion clamping portions 187.

This supporting member 180 supports the film portion 132 such that it clamps the film portion 132 alternately with the plural supporting portions 181 formed along the longitudinal direction. Specifically, the support member 180 supports the film portion 132 entirely by inserting the upper supporting pin 183 into the upper through hole 171 of the film portion 132 and the central portion supporting pins 185 into the central through holes 173, respectively, to fasten them by an ultrasonic welding method and by clamping the root end of the film portion 132 with the lower portion clamping portions 187. When the level detecting element 131 (or the film portion 132) is to be supported by the supporting member 180, the sizes of the supporting member 180 and the level detecting element 131 are so suitably adjusted, although not shown, that the paired parallel reinforcing portions 151 disposed on the film portion 132 may be individually arranged at least partially overlapped by the individual supporting portions 181.

As shown in FIG. 5 and FIG. 6, the base member 121 is provided therein with a wiring circuit board 163, which is electrically connected through the wiring members 161 with the individual electrode terminals 141, 143, 145, 147 and 155 of the level detecting element 131. Moreover, the base member 121 is provided with the connector portion 123, and a connector terminal 165 disposed in the connector portion 123 is electrically connected with the wiring circuit board 163 and further with the not-shown external devices.

The invention has been thus far described in connection with its embodiments. However, the invention should not be limited to the embodiments but can adopt various modes.

For example, the individual sizes of the detecting electrodes, the reference electrodes and the reinforcing portions should not be limited to the aforementioned numerical values but can be suitably set according to various conditions such as the subject to be detected or the environment of installation.

On the other hand, the liquid to be measured should not be limited to the aforementioned oil but may be any liquid having a dielectric constant different from that of air, as exemplified by gasoline or water.

On the other hand, the liquid state detecting element should not be limited, unlike the level detecting element 11 thus far described, to the configuration, in which one film portion is integrally provided with the two sets of detecting electrodes (i.e., the paired detecting electrodes 13 and the paired reference electrodes 17). For example, the first liquid state detecting element having the paired detecting electrodes 13 and the second liquid state detecting element having the paired reference electrodes 17 may also be individually formed by using different film portions so that the liquid state (or the oil level) can be detected by using the first liquid state detecting element and the second liquid state detecting element.

On the other hand, the material making the reinforcing portions should not be limited to copper but may be exemplified by a 42-Ni—Fe alloy or stainless steel.

This application is based on Japanese Patent application JP 2004-1249, filed Jan. 6, 2004, the entire content of which is hereby incorporated by reference, the same as if set forth at length.

What is claimed is:

1. A liquid state detecting element comprising:
   a film portion made of a flexible insulating material and extending in a longitudinal direction; and
   a pair of detecting electrodes juxtaposed to each other on a layer of said film portion and extending in said longitudinal direction,
   in which said detecting electrodes are for being immersed at least partially in a liquid to be measured, so that a state of said liquid is detected on a basis of an electrostatic capacity between said pair of detecting electrodes,
   wherein:
   said liquid state detecting element further comprises reinforcing portions made of a conductive material and disposed on said layer of said film portion on an outer side of said detecting electrodes; and
   said reinforcing portions include:
   a grounding terminal for being connected with a ground line; and
   a pair of parallel reinforcing portions extending in said longitudinal direction along side edges of said film portion so as to sandwich said pair of detecting electrodes.

2. The liquid state detecting element as claimed in claim 1, wherein each of said parallel reinforcing portions has a width size in a width direction perpendicular to said longitudinal direction larger than a width size of each of said detecting electrodes.

3. The liquid state detecting element as claimed in claim 1, wherein said reinforcing portions include a connecting reinforcing portion for connecting individual end portions of said pair of parallel reinforcing portions.

4. The liquid state detecting element as claimed in claim 1, wherein said detecting electrodes and said reinforcing portions are made of the same material.

5. The liquid state detecting element as claimed in claim 1, wherein said liquid state detecting element further comprises a pair of reference electrodes juxtaposed to each other on said layer of said film portion and disposed at a position different in said longitudinal direction from a position of said pair of detecting electrodes; and
   said pair of parallel reinforcing portions are disposed to sandwich said pair of reference electrodes.

6. A liquid state detecting sensor comprising:
   a liquid state detecting element including: a film portion made of a flexible insulating material and extending in a longitudinal direction; a pair of detecting electrodes juxtaposed to each other on a layer of said film portion and extending in said longitudinal direction; and reinforcing portions made of a conductive material and disposed on said layer of said film portion on an outer side than said detecting electrodes; and
   a supporting member for supporting said liquid state detecting element,
   in which, by immersing at least a portion of said liquid state detecting element in a liquid to be measured, said detecting electrodes are immersed at least partially in the measured liquid, so that a state of said measured liquid is detected on a basis of an electrostatic capacity between said pair of detecting electrodes, wherein:
   said supporting member includes supporting portions for supporting a surface and a back face of said film portion, said reinforcing portions include a pair of parallel reinforcing portions extending in said longitudinal direction, and said liquid state detecting element is supported by arranging said pair of parallel reinforcing portions, at least partially overlapped by said supporting portions.

7. The liquid state detecting sensor as claimed in claim 6, wherein:
   said supporting member includes erected pins; and
   said liquid state detecting element includes through holes extending through said film portion, and said liquid state detecting element is positioned on said supporting member by inserting said pins into said through holes.

8. The liquid state detecting sensor as claimed in claim 6, wherein:
   said reinforcing portions include:
   a grounding terminal portion to be connected with a ground line; and
   a pair of parallel reinforcing portions extending in said longitudinal direction along side edges of said film portion so as to sandwich said pair of detecting electrodes.

9. The liquid state detecting sensor as claimed in claim 6, wherein each of said parallel reinforcing portions has a width size in a width direction perpendicular to said longitudinal direction larger than a width size of each of said detecting electrodes.

10. The liquid state detecting sensor as claimed in claim 6, wherein said reinforcing portions include a connecting reinforcing portion for connecting individual end portions of said pair of parallel reinforcing portions.

11. The liquid state detecting sensor as claimed in claim 6, wherein said detecting electrodes and said reinforcing portions are made of the same material.

12. The liquid state detecting sensor as claimed in claim 6, wherein said liquid state detecting sensor further comprises a pair of reference electrodes juxtaposed to each other on said layer of said film portion and disposed at a position different in said longitudinal direction from a position of said pair of detecting electrodes; and
   said pair of parallel reinforcing portions are disposed to sandwich said pair of reference electrodes.

* * * * *